US010137300B2

(12) United States Patent
Bettinger

(10) Patent No.: US 10,137,300 B2
(45) Date of Patent: *Nov. 27, 2018

(54) INGESTIBLE ELECTRICAL DEVICE FOR STIMULATING TISSUES IN A GASTROINTESTINAL TRACT OF AN ORGANISM

(71) Applicant: Carnegie Mellon University, Pittsburgh, PA (US)

(72) Inventor: Christopher J. Bettinger, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/713,525

(22) Filed: Sep. 22, 2017

(65) Prior Publication Data

US 2018/0008825 A1 Jan. 11, 2018

Related U.S. Application Data

(62) Division of application No. 14/397,749, filed as application No. PCT/US2013/038787 on Apr. 30, 2013, now Pat. No. 9,770,588.

(Continued)

(51) Int. Cl.
*A61N 1/36* (2006.01)
*A61N 1/18* (2006.01)
(Continued)

(52) U.S. Cl.
CPC ....... *A61N 1/36007* (2013.01); *A61N 1/0509* (2013.01); *A61N 1/18* (2013.01); *A61N 1/375* (2013.01); *A61N 1/3787* (2013.01)

(58) Field of Classification Search
CPC . A61N 1/36007; A61N 1/0509; A61N 1/0517
See application file for complete search history.

(56) References Cited

U.S. PATENT DOCUMENTS 7,978,064 B2 7/2011 Zdeblick et al.
8,847,766 B2 9/2014 Zdeblick et al.
(Continued)

FOREIGN PATENT DOCUMENTS

WO WO2013165964 11/2013

OTHER PUBLICATIONS

International Search Report and Written Opinion dated Sep. 16, 2013 for Int'l. Appln. No. PCT/US2013/038787 (8 pgs.).
(Continued)

*Primary Examiner* — Joseph Dietrich
(74) *Attorney, Agent, or Firm* — Fish & Richardson P.C.

(57) ABSTRACT

In one aspect, an ingestible, electrical device, comprises one or more electrodes comprising a biocompatible conducting material and a biocompatible insulating material; a generator connected to the one or more electrodes; and an outer casing enclosing the one or more electrodes and the generator, the outer casing configured to dissolve in an aqueous environment of the organism; wherein the one or more electrodes have a first form factor when enclosed in the outer casing and a second form factor following a dissolution of the outer casing, the first form factor is a form factor that is collapsed an increased amount relative to an amount that the second form factor is collapsed, and the second form factor is a form factor that is collapsed a decreased amount relative to an amount that the first form factor is collapsed.

26 Claims, 6 Drawing Sheets

Related U.S. Application Data

(60) Provisional application No. 61/687,720, filed on Apr. 30, 2012.

(51) Int. Cl.
    *A61N 1/375*     (2006.01)
    *A61N 1/05*     (2006.01)
    *A61N 1/378*     (2006.01)

(56) References Cited

U.S. PATENT DOCUMENTS

| | | |
|---|---|---|
| 2002/0198470 A1 | 12/2002 | Imran et al. |
| 2003/0208107 A1 | 11/2003 | Refael |
| 2004/0186530 A1 | 9/2004 | Gluschuk et al. |
| 2007/0238940 A1 | 10/2007 | Amirana |
| 2008/0004671 A1 | 1/2008 | Anderson et al. |
| 2008/0065168 A1 | 3/2008 | Bitton et al. |
| 2008/0275430 A1 | 11/2008 | Belsky et al. |
| 2010/0021536 A1 | 1/2010 | Gross |

OTHER PUBLICATIONS

Office Action in corresponding U.S. Appl. No. 14/397,749, dated Feb. 1, 2016, pp. 1-6.
Response to Office Action in corresponding U.S. Appl. No. 14/397,749, dated Feb. 1, 2016, pp. 1-7, filed Apr. 29, 2016.
Final Office Action in corresponding U.S. Appl. No. 14/397,749, dated Aug. 29, 2016, pp. 1-7.
Response to Final Office Action in corresponding U.S. Appl. No. 14/397,749, dated Aug. 29, 2016, pp. 1-8, filed Nov. 28, 2016.
Office Action in corresponding U.S. Appl. No. 14/397,749, dated Jan. 12, 2017, pp. 1-6.
Response to Office Action in corresponding U.S. Appl. No. 14/397,749, dated Jan. 12, 2017, pp. 1-7, filed Apr. 25, 2017.
Hubert HB et al., "Obesity as an independent risk factor for cardiovascular disease: a 26 year old follow-up of participants in the Framingham Heart Study," Circulation, 67(5):968-977 (1983).
Mokdad AH et al., "Prevalence of Obesity, Diabetes, and Obesity-Related Health Risk Factors," Journal of the American Medical Association, 289(1):76-79 (2003).
Bianchini F. et al., "Overweight, obesity, and cancer risk," The Lancet Oncology, 3(9):565-574 (2002).
Flegal KM et al., "Prevalence and Trends in Obesity Among US Adults," Journal of the American Medical Assocation, 303(3):235-241 (2010).
Whitaker RC, "The Childhood Obesity Epidemic: Lessons for Preventing Socially Determined Health Conditions," Arch Pediatr Adolesc Med, 165(11):973-975 (2011).
Wild SH et al., "Global Prevalence of Diabetes: Estimates for the Year 2000 and Projections for 2030," Diabetes Care, 27(10):2569 (2004).
Hogan P. et al., "Economic Costs of Diabetes in the U.S. in 2002," American Diabetes Association, 2003.
Buchwald H. et al., Journal of the American Medical Association, 292(14):1724-1737 (2004).
Sjostrom L. et al., "Effects of Bariatric Surgery on Mortality in Swedish Obese Subjects," New England Journal of Medicine, 357(8):741-52 (2007).
Qi H et al., "Effects of intestinal electrical stimulation on postprandial small-bowel motility and transit in dogs," American Journal of Surgery, 192(5):e55-e60 (2006).
Hasler WL et al., "Methods of gastric electrical stimulation and pacing: a review of their benefits and mechanisms of action in gastroparesis and obesity," Neurogastroenterology & Motility, 21(3):229-43 (2009).
McCallum RW et al., "Gastric Electrical Stimulation with Enterra Therapy Improves Symptoms From Diabetic Gastroparesis in a Prospective Study," Clinical Gastroenterology and Hepatology, 8(11):947-54.e1 (2010).

Schlaepfer TE et al., "Vagus nerve stimulation for depression: efficacy and safety in a European study," Pyschological Medicine, 38(05):651-61 (2008).
Schachter SC et al., "Vagus Nerve Stimulation," Epilepsia, 39(7):677-86 (1998).
Rosas-Ballina M. et al., "Acetylcholine-Synthesizing T Cells Relay Neural Signals in a Vagus Nerve Circuit," Science, 334(6052):98-101 (2011).
Helmers SL et al., "Vagus Nerve Stimulation Therapy in Pediatric Patients with Refractory Epilepsy: Retrospective Study," Journal of Child Neurology, 16(11):843-8 (2001).
Elliott RE et al., "Efficacy of vagus nerve stimulation over time: Review of 65 consecutive patients with treatment-resistant epilepsy treated with VNS>10 years," Epilepsy & Behavior, 20(3):478-83 (2011).
Wang G-J et al., "Gastric stimulation in obese subjects activates the hippocampus and other regions involved in brain reward circuitry," PNAS, 103(42):15641-5 (2006).
Zhu H. et al., "Implantable Gastric Stimulation Inhibits Gastric Motility via Sympathetic Pathway in Dogs," Obesity Surgery, 15(1):95-100 (2005).
Inui A. et al., "appetite, and gastric motility: the emerging role of the stomach as an endocrine organ," FASEB Journal, 18(3):439-56 (2004).
Murphy KG et al., "Gut hormones and the regulation of energy homeostasis," Nature, 444(7121):854-9 (2006).
Tschop M et al., "Ghrelin induces adiposity in rodents," Nature, 407(6806):908-13 (2000).
Zhang JV et al., "Obestatin, a Peptide Encoded by the Ghrelin Gene, Opposes Ghrelin's Effects on Food Intake," Science, 310(5750):996-9 (2005).
Moran TH et al., "Gastrointestinal satiety signals II," Cholecystokinin American Journal of Physiology Gastrointest Liver Physiology, 286(2):G183-G8 (2004).
Hanusch-Enserer U et al., "News in gut-brain communication: a role of peptide YY (PYY) in human obesity and following bariatric surgery?," European Journal of Clinical Investigation, 35(7):425-30 (2005).
Batterham RL et al., "Gut hormone PYY3-36 physiologically inhibits food intake," Nature 418(6898):650-654 (2002).
Xu J. et al., "Gastric/Intestinal Electrical Stimulation Modulates Appetite Regulatory Peptide Hormones in the Stomach and Duodenum in Rats," Obesity Surgery, 17(3):406-13 (2007).
Sallam HS et al., "Colon Electrical Stimulation: Potential Use for Treatment of Obesity," Obesity, 19(9):1761-7 (2011).
Xu X et al., "Pyloric electrical stimulation reduces food intake by inhibiting gastric motility in dogs," Gastroenterology, 128(1):43-50 (2005).
Cigaina V et al., "Gastric Pacing for Morbid Obesity: Plasma Levels of Gastrointestinal Peptides and Leptin," Obesity, 11(12):1456-62 (2003).
Sanmiguel CP et al., "Gastric Electrical Stimulation with the Tantalus® System in Obese Type 2 Diabetes Patients: Effect on Weight and Glycemic Control," Journal of Diabetes Science and Technology, 3(4):964-70 (2009).
Kashyap P et al., "Diabetic gastroparesis: what we have learned and had to unlearn in the past 5 years," Gut, 59(12):1716-26 (2010).
McCallum RW et al., "Mechanisms of symptomatic improvement after gastric electrical stimulation in gastroparetic patients," Neurogastroenterology & Motility, 22(2):161-e51 (2010).
Yin J et al., "Gastric Neuromodulation with Enterra System for Nausea and Vomiting in Patients with Gastroparesis," Neuromodulation: Technology at the Neural Interface, 2012.
Zhang J. et al., "Gastric electrical stimulation parameter dependently alters ventral medial hypothalamic activity and feeding in obese rats," Neuroregulation and Motility, 301(5)G912-G8 (2011).
Shikora S. et al., "Impantable Gastric Stimulation for the Treatment of Severe Obesity," Obesity Surgery, 14(4):545-8 (2004).
Cigaina V., "Gastric Pacing as Therapy for Morbid Obesity: Preliminary Results," Obesity Surgery, 12(Supplement 1):12-16 (2002).

(56) References Cited

OTHER PUBLICATIONS

Scott AS, "What are you Yanks Doing?" The U.S. Experience with Implantable Gastic Stimulation (IGS) for the Treatment of Obesity-Update on the Ongoing Clinical Trials, Obesity Surgery, 14(Supplement 1):40-48 (2004).

Hu WJ et al., "Molecular basis of biomaterial-mediated foreign body reactions," Blood, 98(4):1231-8 (2001).

Luttikhuizen DIT et al., "Cellular and molecular dynamics in the foreign body reaction," Tissue Engineering, 12(7):1955-70 (2006).

Keselowsky BG et al., "Role of plasma fibronectin in the foreign body response to biomaterials," Biomaterials, 28(25):3626-31 (2007).

Engelsman AF et al., "Antimicrobial effects on an No-releasing poly(ethylene vinylacetate) coating on soft-tissue implants in vitro and in murine model," Acta Biomaterialia, 5(6):1905-10 (2009).

Costerton JW et al., "Biofilm in implant infections: Its production and regulation," Milano Italie:Wichtig 2005.

Nagata M et al., "Biodegradable and photocurable multiblock copolymers with shape-memory properties from poly($\epsilon$-caprolactone) diol, poly(ethylene glycol), and 5-cinnamoyloxyisophthalic acid," Journal of Applied Polymer Science, 120(6):3556-64 (2011).

Lu XL et al., "Shape memory effects of poly(L-lactide) and its copolymer with poly($\epsilon$-caprolactone)," Polymer Bulletin, 58(2):381-91 (2007).

Mather PT et al., "Shape Memory Polymer Research," Annual Review of Materials Research, 39(1):445-71 (2009).

Farra R et al., "First-in-Human Testing of a Wirelessly Controlled Drug Delivery Microchip," Science Translational Medicine, 4(122):122ra21 (2012).

Bowden N. et al., "Spontaneous formation of ordered structures in thin films of metals supported on an elastomeric polymer," Nature, 393(6681):146-9 (1998).

Bowden N. et al., "The controlled formation of ordered, sinusoidal structures by plasma oxidation of an elastomeric polymer," App Phys Lett. 75(17):2557-9 (1998).

(a)

(b)

(c)

(d)

(e)

INGESTIBLE ELECTRICAL DEVICE FOR STIMULATING TISSUES IN A GASTROINTESTINAL TRACT OF AN ORGANISM

CLAIM OF PRIORITY

This application is a divisional application and claims the benefit of priority under 35 U.S.C. § 121 to U.S. patent application Ser. No. 14/397,749, filed on Oct. 29, 2014, which is a U.S. National Stage Application under 35 U.S.C. § 371 of and claims priority to International Application Number PCT/US2013/038787, filed on Apr. 30, 2013, which claims the benefit of priority under 35 U.S.C. § 119(e) to provisional U.S. Patent Application No. 61/687,720, filed on Apr. 30, 2012, the entire contents of each of which are hereby incorporated by reference.

FIELD OF USE

The present disclosure relates generally to an ingestible, electrical device, and specifically to an electrical device that stimulates tissues of a gastrointestinal tract of an organism.

BACKGROUND

In gastric bypass surgery, a surgeon reduces the volume of the stomach by suturing off a large section of the stomach. A portion of the small intestine is then resected, and the remaining organ structure is ligated to the stomach. The result of this therapy is that the amount of food that patients may consume at one time is restricted and the allowed time for nutrient absorption is dramatically reduced. Although effective, this procedure produces debilitating and dangerous side effects such as malnutrition and death.

SUMMARY

The present disclosure describes apparatus and methods relating to an ingestible, electrical device that stimulates tissues of a gastrointestinal tract of an organism. The device includes a stimulation electrode that provides a current, a voltage, or both to the tissue of the organism and a component for generating the current, the voltage, or both.

In one aspect of the present disclosure, an ingestible, electrical device, comprises one or more electrodes comprising a biocompatible conducting material and a biocompatible insulating material; a generator connected to the one or more electrodes, with the generator being configured to deliver one or more of a current or a voltage across the one or more electrodes to stimulate one or more internal cells of an organism that ingests the ingestible, electrical device; and an outer casing enclosing the one or more electrodes and the generator, the outer casing configured to dissolve in an aqueous environment of the organism; wherein the one or more electrodes have a first form factor when enclosed in the outer casing and a second form factor following a dissolution of the outer casing, wherein the first form factor is a form factor that is collapsed an increased amount relative to an amount of that the second form factor is collapsed, and wherein the second form factor is a form factor that is collapsed a decreased amount relative to an amount that the first form factor is collapsed.

Implementations of the disclosure can include one or more of the following features. The one or more electrodes may include a complementary anode cathode pair. The biocompatible conducting material may include at least one of a bioinert metal or a conducting polymer. The bioinert metal may include at least one of copper, gold, magnesium, silver, platinum, or zinc. The biocompatible insulating material may include a bioexcretable copolymer. The bioexcretable copolymer comprises at least one of polyester, polyanhydride, polyamide, polyether, polyphosphoester, polyorthoester, poly(ε-caprolactone) (PCL), or poly(ethylene glycol) (PEG). In some implementations, the generator includes a water-activated battery comprising one or more biocompatible materials. In some implementations, the generator includes a receiver coil and a rectifying circuit, each of the receiver coil and the rectifying circuit comprising one or more of a biodegradable material and a bioinert metal, the receiver coil configured to receive a near-field radio frequency signal, and the rectifying circuit configured to convert energy from the near-field radio frequency signal into the one or more of the current or the voltage. In some implementations, the generator includes one or more fuel cells. The generator may be configured to provide up to 0.1 mA of current for up to 90 minutes. The outer casing comprises at least one of gelatin, synthetic alphahydroxy polymer, crosslinked carbohydrate, polyester, polyanhydride, polyamide, polyether, polyphosphoester, polyorthoester, poly($\square$-caprolactone) (PCL), or poly(ethylene glycol) (PEG). A timing of the dissolution of the outer casing may be based on a thickness of and a degree of crosslinking within a material of the outer casing. The ingestible, electrical device may be an electrical device that stimulates one or more internal cells of a gastrointestinal tract of the organism. The first form factor of the one or more electrodes may be formed by configuring the one or more electrodes into a planar geometry and straining the one or more electrodes equibiaxially during deposition of the bioinert metal to promote thin film metallic buckling of the one or more electrodes.

In another aspect of the present disclosure, a method performed by an ingestible, electrical device, comprises following a dissolution of an outer casing of the ingestible, electrical device, expanding a form factor of one or more electrodes included in the ingestible, electrical device; wherein at least one of the one or more electrodes comprises a biocompatible conducting material and a biocompatible insulating material; and wherein the dissolution occurs in an organism that ingests the ingestible, electrical device; activating, based on exposure to an aqueous environment in the organism, a generator of the ingestible, electrical device, the generator being connected to the one or more electrodes; following activation of the generator, delivering one or more of a current or a voltage across the one or more electrodes of the ingestible, electrical device; stimulating, based on delivery of the one or more of the current or the voltage, one or more internal cells of the organism that ingests the ingestible, electrical device; and ceasing to deliver the one or more of the current or the voltage across the one or more electrodes after a predetermined time; wherein the ingestible, electrical device may be configured to break down following a cease in delivery of the one or more of the current or the voltage.

Implementations of the disclosure can include one or more of the following features. The method includes causing, based on stimulating, a decrease in an amount of intestinal motility in the organism relative to an amount of intestinal motility in the organism prior to stimulation. The ingestible, electrical device may be an electrical device that stimulates one or more internal cells of a gastrointestinal tract of the organism. The biocompatible conducting material may include at least one of a bioinert metal or a conducting polymer. The bioinert metal may include at least one of copper, gold, magnesium, silver, platinum, or zinc. The biocompatible insulating material may include a bioexcretable copolymer. The bioexcretable copolymer may include at least one of polyester, polyanhydride, polyamide, polyether, polyphosphoester, polyorthoester, poly(-caprolactone) (PCL) or poly(ethylene glycol) (PEG). In some implementations, the generator includes a water-activated battery comprising biocompatible materials. In some implementations, the generator includes a receiver coil and a rectifying circuit, each of the receiver coil and the rectifying circuit comprising one or more of a biodegradable material and a bioinert metal, the receiver coil configured to receive a near-field radio frequency signal, and the rectifying circuit configured to convert energy from the near-field radio frequency signal into the one or more of the current or the voltage. In some implementations, the generator includes one or more fuel cells. The generator may be configured to provide up to 0.1 mA of current for up to 90 minutes. The outer casing may include at least one of a gelatin material, a synthetic alphahydroxy polymer, a crosslinked carbohydrate, polyester, polyanhydride, polyamide, polyether, polyphosphoester, polyorthoester, poly(-caprolactone) (PCL), or poly(ethylene glycol) (PEG). A timing of the dissolution of the outer casing may be based on a thickness of and a degree of crosslinking within a material of the outer casing.

In yet another aspect of the present disclosure, a gastro-electrical stimulation (GES) device, comprises one or more electrodes comprising gold deposited on a poly(ε-caprolactone) (PCL) and poly(ethylene glycol) (PEG) copolymer, the one or more electrodes configured to stimulate one or more internal cells of an organism that ingests the GES device to cause a decrease in an amount of intestinal motility in the organism relative to an amount of intestinal motility in the organism prior to stimulation; a water-activated battery comprising one or more biocompatible materials, the water-activated battery connected to the one or more electrodes, with the water-activated battery being configured to deliver a current of up to 0.1 mA for up to 90 minutes across the one or more electrodes to stimulate the one or more internal cells of the organism that ingests the GES device; and an outer casing comprising gelatin material in a capsule form, the outer casing enclosing the one or more electrodes and the water-activated battery, the outer casing configured to dissolve in an aqueous environment of the organism, with a timing of a dissolution of the outer casing based on a thickness and a degree of crosslinking within the gelatin material; wherein the electrodes have a first form factor when enclosed in the outer casing and a second form factor following the dissolution of the outer casing, wherein the first form factor is a form factor with an decreased amount of expansion relative to an amount of expansion of the second form factor, and wherein the second form factor is a form factor with an increased amount of expansion relative to an amount of expansion of the first form factor.

The details of one or more implementations are set forth in the accompanying drawings and the description below. Other features, objects, and advantages will be apparent from the description, the drawings, and the claims.

DETAILED DESCRIPTION

An ingestible, electrical device consistent with this disclosure may provide GES that can be administered orally. The ingestible, electrical device may include a stimulation electrode and a generator. The generator provides a current, a voltage, or both to the stimulation electrode to stimulate tissues of a gastrointestinal (GI) tract of an organism. In this context, stimulate includes a change in local properties based on a delivery of a voltage or a current. The device poses minimal risk to an organism, especially in the context of consuming the device for chronic management of obesity. While this disclosure describes an ingestible, electrical device in the context of coordinated simulation for obesity treatment, the apparatus and methods described in the present disclosure could also be used to treat a wide range of food metabolism pathologies.

The ingestible, electrical device may be fabricated into a form factor that can be delivered orally and easily swallowed. The ingestible, electrical device may be fabricated from materials that are biodegradable and endogenous to an organism that ingests the device. Biodegradable devices reduce the risk associated with permanent devices including possible build-up and obstruction in the GI tract. Additionally, finite device lifetimes limit the potential toxicity profile associated with ingesting multiple devices over a sustained period of time.

Figure 1:
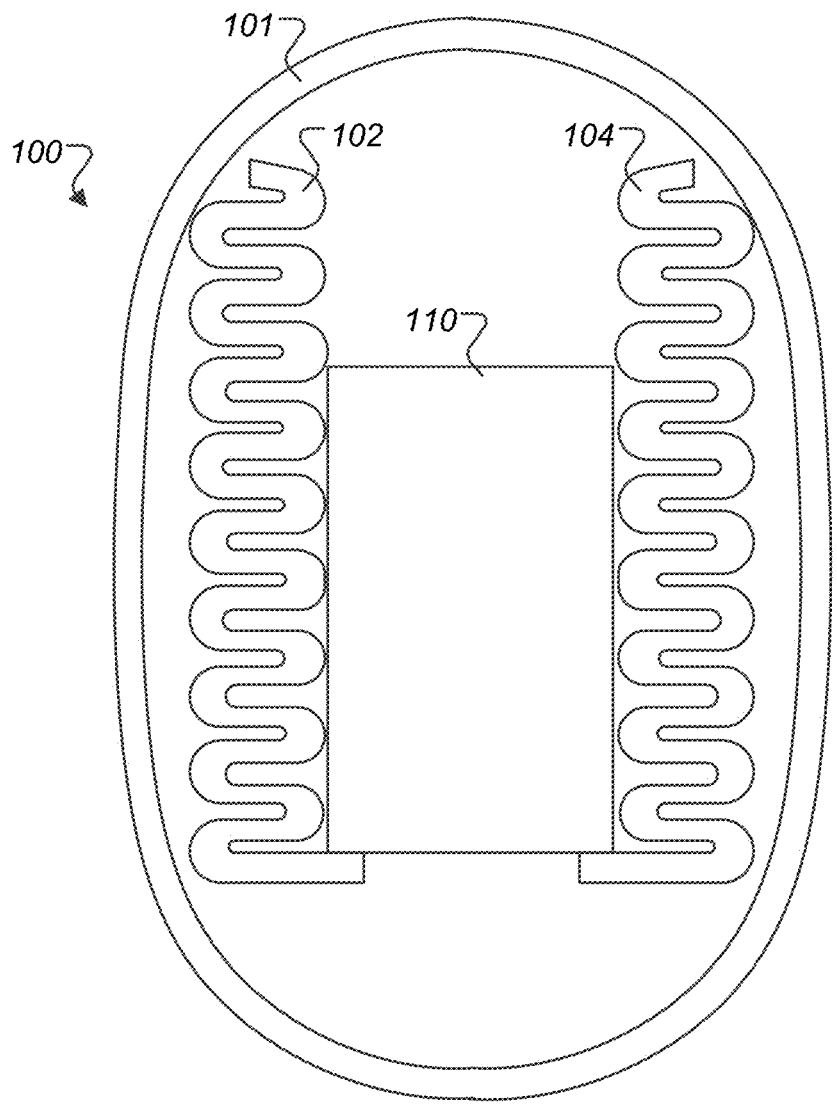
FIG. 1 shows an example of an ingestible, electrical device in a condensed geometry packaged into an orally ingestible capsule.

FIG. 1 shows an example of an ingestible, electrical device 100 in a condensed (consolidated, compressed, or collapsed) geometry packaged into an orally ingestible capsule. When packaged in an outer casing 101, the device 100 may take the approximate shape of a rectangular prism with a length of 2 cm, a width of 0.8 cm, and a height of 0.8 cm, which is approximately the size of a large pill to be taken orally. The device 100 includes non-toxic materials that can be absorbed, metabolized, or excreted by an organism, e.g., a human or other animal, that ingests the device 100. FIG. 1 will be described in conjunction with FIG. 2, which shows the ingestible, electrical device 100 in an expanded (or swollen) geometry with deployed electrodes 102, 104, 106, and 108. In addition to the electrodes 102, 104, 106, and 108, the device 100 includes a generator 110.

The outer casing 101 encloses the device components, such as the electrodes 102, 104, 106, and 108, and the generator 110. The outer casing 101 may protect the device components as the device 100 passes through a stomach and into a small intestine of an organism to ensure that the device 100 is not subjected to caustic environments. The outer casing may serve as a time protective retainer that keeps the electrodes 102, 104, 106, and 108 in the condensed geometry until it reaches an area of interest within the GI tract of the organism. The material of the outer casing 101 can be engineered to dissolve within a precisely defined time line. After dissolution, the outer casing 101 can be absorbed and metabolized by the organism, or excreted by the organism with other non-absorbed device components.

The outer casing 101 of the device 100 may include, for example, gelatin in a capsule form similar to those commonly used in existing oral pill formulations. The timing of the device expansion or swelling is controlled by engineering the thickness and degree of crosslinking within the gelatin layer. The outer casing 101 may include other suitable materials such as synthetic alpha-hydroxy polymers, crosslinked carbohydrates, polyesters, polyanhydride, polyamides, polyethers, polyphosphoesters, polyorthoesters, poly(ε-caprolactone) (PCL), or poly(ethylene glycol) (PEG).

Figure 2:
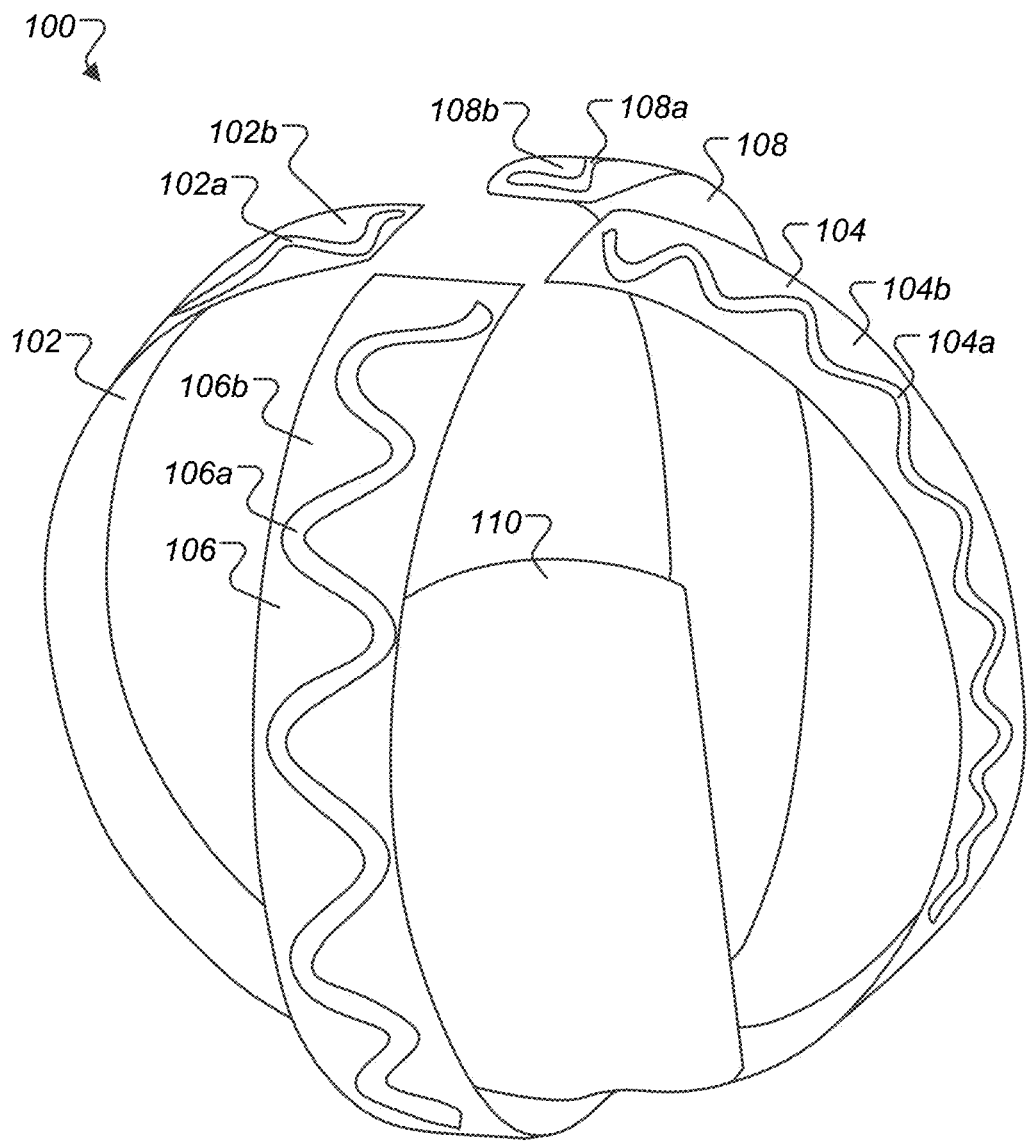
FIG. 2 shows the ingestible, electrical device of FIG. 1 in an expanded geometry with deployed electrodes.

The electrodes 102, 104, 106, and 108 have a condensed geometry when packaged in the outer casing 101 as shown in FIG. 1, and have an expanded or swollen geometry following dissolution of the outer casing 101 as shown in FIG. 2. The electrodes 102, 104, 106, and 108 may include conducting materials 102*a*, 104*a*, 106*a*, and 108*a* such as bioinert metals or conducting polymers. Examples of bioinert metals include copper, gold, magnesium, silver, platinum, and zinc.

The electrodes 102, 104, 106, and 108 may be shape-memory electrodes fabricated from insulating materials 102*b*, 104*b*, 106*b*, and 108*b* such as copolymers based on poly(ε-caprolactone) (PCL), poly(ethylene glycol) (PEG), or a combination. PCL and PEG copolymers are thermally actuated to deploy the electrodes 102, 104, 106, and 108 through expansion. PCL is biodegradable, and PEG is bio-excretable. PCL and PEG have both been extensively utilized in medical devices that have been FDA-approved for various applications as surgical materials, drug delivery systems, and scaffolds for tissue regeneration. The electrodes 102, 104, 106, and 108 may include other suitable insulating materials such as polyesters, polyanhydride, polyamides, polyethers, polyphosphoesters, polyorthoesters, or a combination. Poly(ester amide) networks are both elastomeric and biodegradable. Biodegradable shape-memory elastomer electrodes synthesized from poly(ester amide) networks can be actuated through rubbery-glassy transitions via hydration to deploy the electrodes 102, 104, 106, and 108 through swelling. Another example of a suitable material for the electrodes 102, 104, 106, and 108 may include a superabsorbent polymer such as a hydrogel. In this example, the electrodes 102, 104, 106, and 108 may deploy by swelling due to hydrolysis. Other mechanisms for deployment of the electrodes 102, 104, 106, and 108 may be based on environmental factors such as changes in potential hydrogen (pH), changes in temperature, and other environmental factors.

The generator 110 is connected to the electrodes 102, 104, 106, and 108 to provide a current, a voltage, or both to the electrodes 102, 104, 106, and 108. The generator 110 may be composed of non-toxic biomaterials that can be absorbed as nutrients or excreted as waste. The generator 110 may be an on-board power supply for autonomous power generation or electronically active structures that are able to harvest externally applied energy which can be converted into electric current, voltage, or both for tissue stimulation. For example, the device 100 can be powered internally through a biocompatible or biodegradable battery or externally through near-field radiofrequency power transfer. The generator 110 may be configured to provide, for example, up to 0.1 mA of current for up to 90 minutes. The current or voltage may be programmed into arbitrary wave forms including constant, pulsed, and sinusoidal stimulation patterns. The current or voltage can be alternating or direct.

In some implementations, the generator 110 may be a water-activated biodegradable battery. The low currents and voltages and limited stimulation times of the device 100 allow for incorporation of a small battery to serve as an on-board power supply. The geometry of the battery may be a high-aspect ratio cylinder similar to an oral pill. The battery may be stored in a dry state and coated in a biodegradable poly(L-lactide-co-glycolide) (PLGA) film that is semi-permeable to water. Battery operation is activated once water permeates the PLGA film and wets the aqueous cell. The initiation of battery function is engineered by controlling water permeation in the PLGA casing. Water permeability is controlled through PLGA composition and film geometry. Other suitable material compositions may be used in addition, or as an alternative, to the PLGA film.

The battery may include a cathode, an anode, and a separator. The cathode may be fabricated from a compound based on sodium and manganese oxide. These cathode materials are able to shuttle sodium ions in aqueous cells with sufficient efficiencies. These cathode materials may be biocompatible. The anode of the battery may be fabricated from activated carbon. Activated carbon is non-toxic and may absorb toxins to replace liver function. The separator may be fabricated from microporous poly(L-lactide). The microporous structure may be achieved by phase inversion via rapid precipitation. The cathode and the anode of the battery are connected to the electrodes 102, 104, 106, and 108.

In some implementations, the generator 110 may power the device is through external radiofrequency stimulation. The generator 110 may include a receiver coil and a rectifying circuit. The receiver coil receives a near-field radio frequency signal, e.g., an AC signal, that may be provided by a pack of external coils. The rectifying circuit converts the energy from the near-field radio frequency signal into electric current, e.g., a DC current, or voltage that is used for GES. The receiver coil and the rectifying circuit may include electronically active biodegradable materials, bioinert metals, or a combination. The generator 110 may be devices other than those described above. For example, the generator 110 may be one or more fuel cells that provide power to the device 100.

Figure 3:
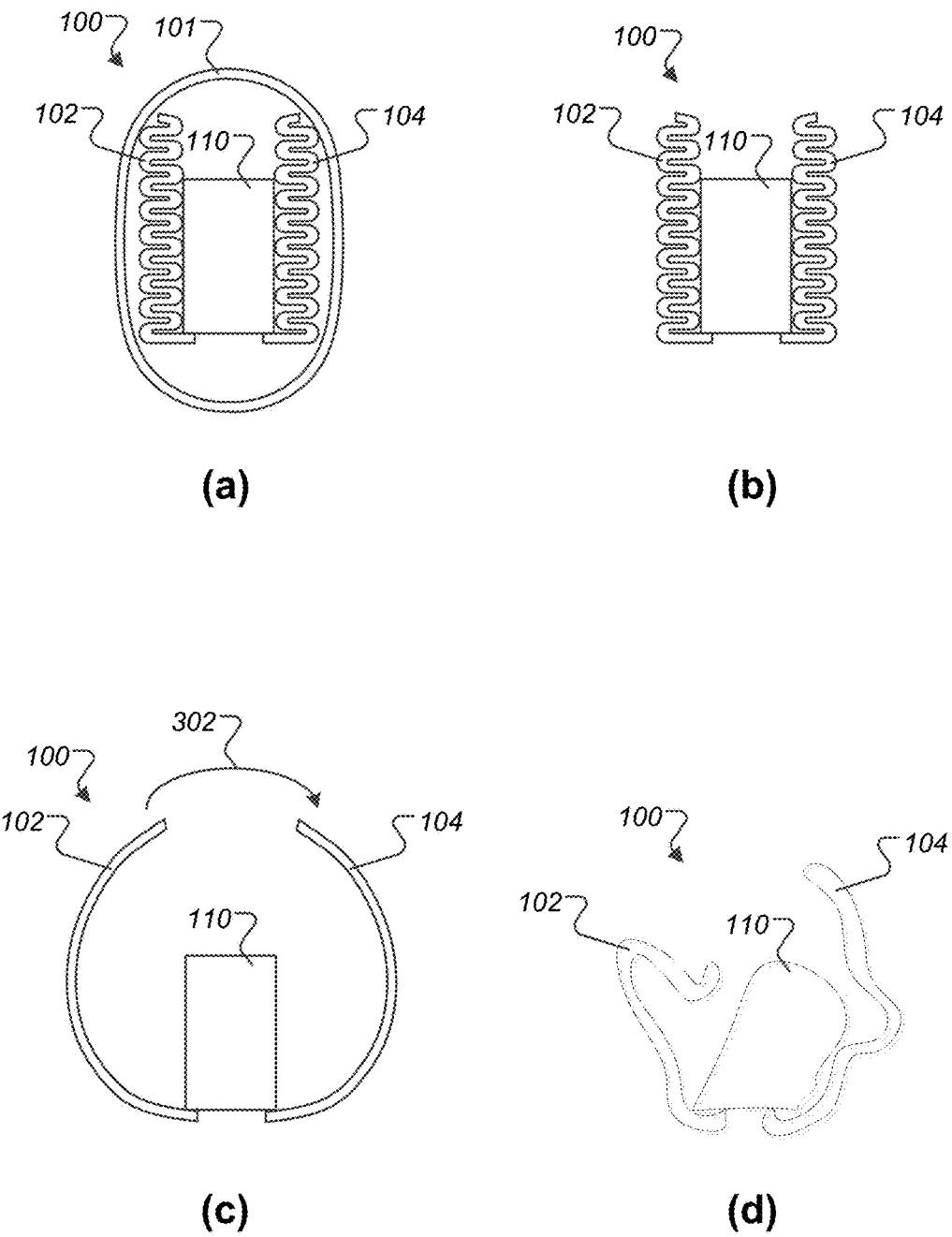
FIG. 3 shows an ingestible, electrical device during different stages of operation.
Figure 4:
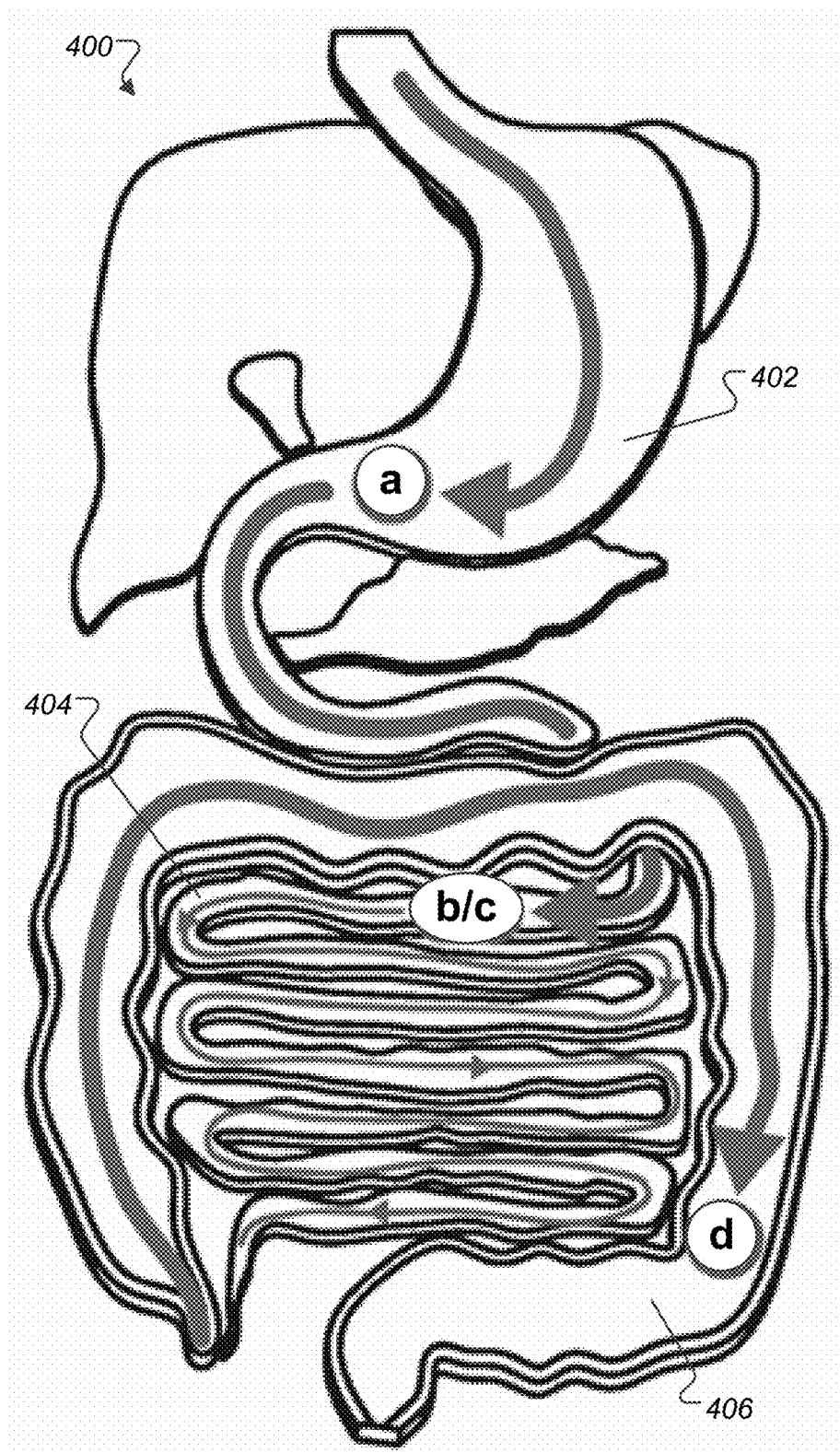
FIG. 4 shows a progression of an ingestible, electrical device through a gastrointestinal tract of an organism.

FIG. 3 shows an ingestible, electrical device, e.g., the device 100 of FIG. 1 and FIG. 2, during different stages (a)-(d) of operation. FIG. 3 will be described in conjunction with FIG. 4, which shows a progression of the device 100 through a gastrointestinal (GI) tract 400 of an organism during the different stages (a)-(d) of operation. The device 100 progresses through the GI tract 400 in a consolidated form factor via natural digestion. The device 100 can be selectively deployed and activated anywhere within the GI tract 400 through careful selection of materials and design of a geometry of the device 100. For example, rapidly dissolvable packaging materials may be suitable for device deployment in a section of the small intestines 404, e.g., the duodenum, while more slowly degrading materials may be suitable for device deployment in a section of the large intestines 406 such as the colon.

In stage (a), the components of the device 100 are enclosed in and protected by the outer casing 101, and the device 100 is inactive. In this context, inactive refers to not being functional as in the case when the generator 110 is not supplying power to the electrodes 102, 104, 106, and 108 of the device 100. The device 100 may be in stage (a) while the device 100 is passing through a stomach 402 and into a small intestine 404 of the organism. The outer casing 101 can be engineered to dissolve within a precisely defined time line. Precisely timed dissolution of the outer casing 101 liberates the device 100 in a predetermined location with the GI track 400.

The device 100 progresses to stage (b) after the device 100 passes through the stomach 402 and into the small intestine 404 of the organism. The outer casing 101 may have completely dissolved after passing through the stomach 404. After dissolution of the outer casing 101, the components of the device 100 are exposed to high salinity aqueous environments with elevated temperatures within the small intestine 404 of the organism.

At stage (c), elevated temperatures and hydration initiate shape change routines in the electrodes 102, 104, 106, and 108. The electrodes 102, 104, 106, and 108 deploy by expanding, unfurling, or swelling. Water diffuses across a polymeric casing of the generator 110 and initiates activation of the generator 110. In the case where the generator 110 is a water-activated battery, hydration of the battery initiates activation of the wet cell. The battery transitions from an inactive dehydrated state into an active wet-cell battery. The generator 110 delivers a current, a voltage, or both 302 across complementary cathode anode electrode pairs, e.g., electrodes 102 and 104, or electrodes 106 and 108. Complementary cathode anode electrode pairs form intimate contact with the soft tissues in the small intestines 404 to stimulate the gastric tissues at the predetermined location of interest. GES may occur for approximately 60 to 120 minutes. In some implementations, the device 100 may continue to progress through the small intestines 404 during GES. In some implementations, the electrodes 102, 103, 106, and 108 may stabilize and anchor the device 100 and retard passage of the device 100 through the GI tract 400 during GES.

After stimulation, the device 100 ceases to function. The device 100, including the electrodes 102, 104, 106, and 108, and the generator 110, may degrade, or break down, and may lose mechanical resiliency at stage (d) as it progresses toward the end of the large intestine 406 of the GI tract 400. The materials of the device 100 are absorbed or metabolized, or passed through the remainder of the GI tract 400 through active digestive motion and eventually excreted. The materials of the device 100 are selected such that they can be completely bioabsorbed by the organism or efficiently secreted without any negative health impacts.

Figure 5:
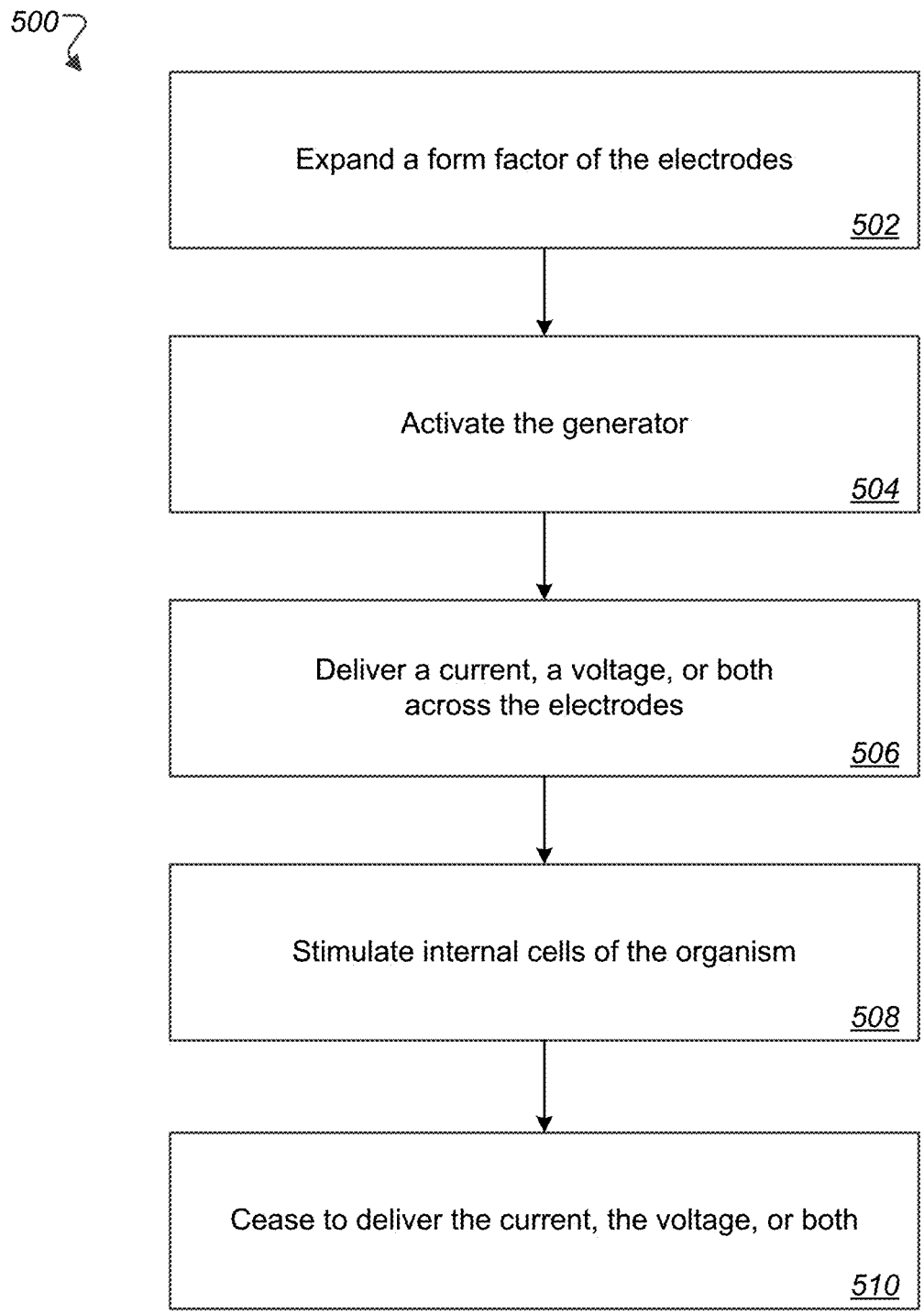
FIG. 5 is a flowchart of operations performed by an ingestible, electrical device.

FIG. 5 is a flowchart of operations performed by an ingestible, electrical device. As described above, the process 500 includes expanding a form factor of one or more electrodes included in the device (502), activating a generator of the device based on exposure to an aqueous environment in the organism (504), and delivering a current, a voltage, or both across the electrodes of the device following activation of the generator (506). Based on delivery of the current, the voltage, or both across the electrodes, the device stimulates one or more internal cells of the organism (508), which may cause a decrease in an amount of intestinal motility in the organism relative to an amount of intestinal motility in the organism prior to stimulation. After a predetermined time of stimulation, the device ceases to deliver the current or the voltage across the electrodes. Following a cease in the delivery of the current or the voltage, the device is configured to degrade or break down.

Figure 6:
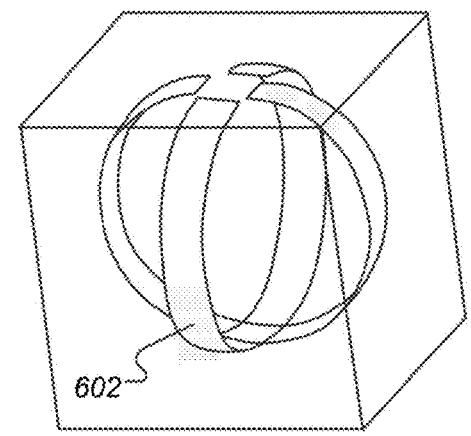
FIG. 6 shows an ingestible, electrical device during different stages of fabrication.
Figure 6:
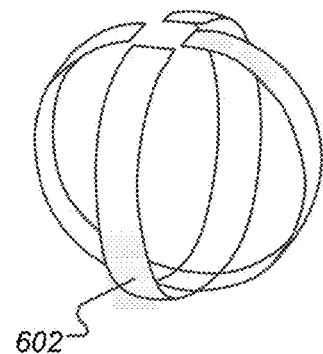
Figure 6:
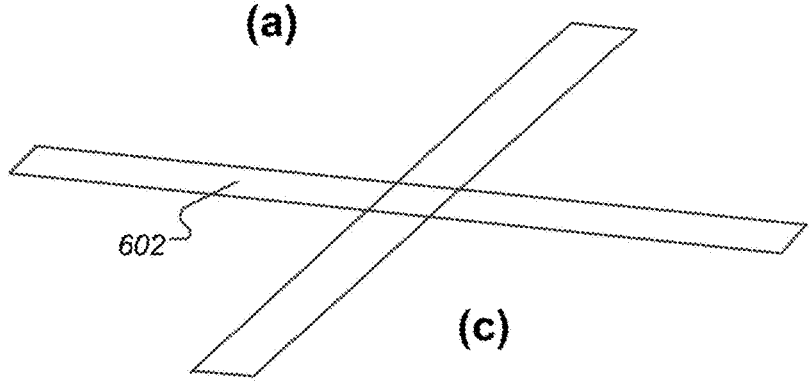
Figure 6:
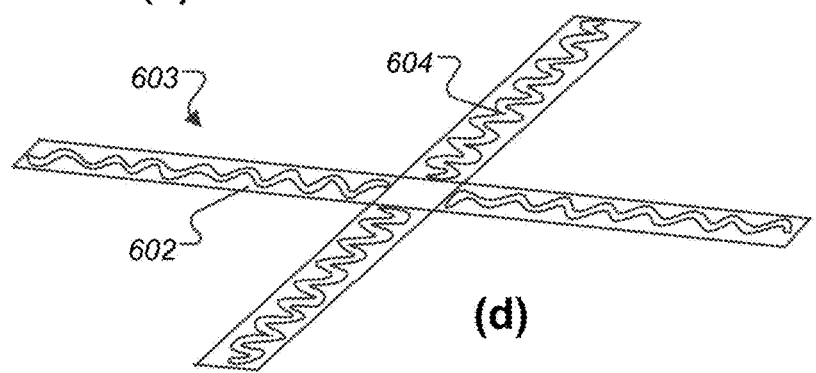
Figure 6:
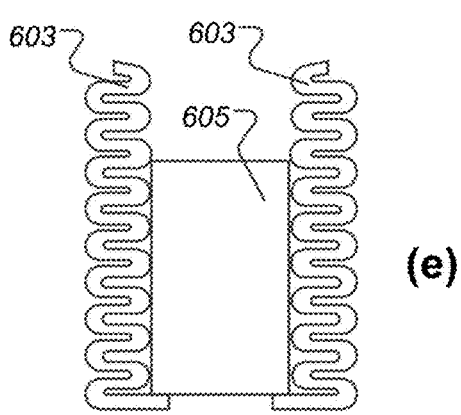

FIG. 6 shows an ingestible, electrical device during different stages of fabrication. The device may be fabricated entirely from non-toxic materials, biodegradable materials, or a combination of both. In some implementations, the device components are fabricated using materials that have been incorporated into FDA-approved medical devices. In some implementations, the device components are fabricated using materials that may be used in dietary supplements or other oral treatments such as detoxification.

In the example of FIG. 6, insulating materials 602, e.g., biodegradable shape-memory polymers synthesized from PCL and PEG composites, are injection molded at stage (a) into a final complex 3D geometry, as shown in stage (b). The form factor of the insulating materials 602 is programmed into a planar geometry at stage (c) to facilitate electrode integration. Materials such as poly(ester) amides can be integrated with an electrically conducting material 604, e.g., a thin gold film. Gold is a bioinert metal that has been used in many medical devices and should pose no risk as a material that is consumed orally. Other suitable conducting materials include other bioinert metals, such as silver and platinum, and conducting polymers. Electrodes 603 are fabricated by thermal deposition or evaporation of the conducting material 604 and patterned using shadow masks at stage (d). At stage (e), the electrodes 603 may be processed into serpentine geometries to enable high density packaging into an outer gelatin capsule. For example, the insulating materials 602 in the planar form factor may be strained equibiaxially during deposition of the conducting material 604 in order to induce thin film buckling. Evaporating rigid films on pre-strained substrates can produce micron-scale buckling features. These corrugated features may help maintain electrical conductivity during deformation of the biodegradable elastomeric electrodes 602 during both packaging and deployment, e.g., during flexion and hydration-induced swelling in the GI tract. The electrodes 603 are connected to a generator 605.

A number of implementations have been described. Nevertheless, various modifications can be made without departing from the spirit and scope of the processes and techniques described herein. In addition, the processes depicted in the figures do not require the particular order shown, or sequential order, to achieve desirable results. In addition, other steps can be provided, or steps can be eliminated, from the described processes, and other components can be added to, or removed from, the describe apparatus and systems. Accordingly, other embodiments are within the scope of the following claims.

What is claimed is:

1. A method performed by an ingestible, electrical device, comprising:
   following a dissolution of an outer casing of the ingestible, electrical device, expanding a form factor of one or more electrodes included in the ingestible, electrical device;
   wherein at least one of the one or more electrodes comprises a biocompatible conducting material and a biocompatible insulating material; and
   wherein the dissolution occurs in an organism that ingests the ingestible, electrical device;
   activating, based on exposure to an aqueous environment in the organism, a generator of the ingestible, electrical device, the generator being connected to the one or more electrodes;
   following activation of the generator, delivering one or more of a current or a voltage across the one or more electrodes of the ingestible, electrical device;
   stimulating, based on delivery of the one or more of the current or the voltage, one or more internal cells of the organism that ingests the ingestible, electrical device; and
   ceasing to deliver the one or more of the current or the voltage across the one or more electrodes after a predetermined time;

wherein the ingestible, electrical device is configured to break down following a cease in delivery of the one or more of the current or the voltage.

2. The method of claim 1, further comprising:
causing, based on stimulating, a decrease in an amount of intestinal motility in the organism relative to an amount of intestinal motility in the organism prior to stimulation.

3. The method of claim 1, wherein the ingestible, electrical device is an electrical device that stimulates one or more internal cells of a gastrointestinal tract of the organism.

4. The method of claim 1, wherein the biocompatible conducting material comprises at least one of a bioinert metal or a conducting polymer.

5. The method of claim 4, wherein the bioinert metal comprises at least one of copper, gold, magnesium, silver, platinum, or zinc.

6. The method of claim 1, wherein the biocompatible insulating material comprises a bioexcretable copolymer.

7. The method of claim 6, wherein the bioexcretable copolymer comprises at least one of polyester, polyanhydride, polyamide, polyether, polyphosphoester, polyorthoester, poly($\varepsilon$-caprolactone) (PCL) or poly(ethylene glycol) (PEG).

8. The method of claim 1, wherein the generator comprises a water-activated battery comprising biocompatible materials.

9. The method of claim 1, wherein the generator comprises a receiver coil and a rectifying circuit, each of the receiver coil and the rectifying circuit comprising one or more of a biodegradable material and a bioinert metal, the receiver coil configured to receive a near-field radio frequency signal, and the rectifying circuit configured to convert energy from the near-field radio frequency signal into the one or more of the current or the voltage.

10. The method of claim 1, wherein the generator comprises one or more fuel cells.

11. The method of claim 1, wherein the generator is configured to provide up to 0.1 mA of current for up to 90 minutes.

12. The method of claim 1, wherein the outer casing comprises at least one of a gelatin material, a synthetic alphahydroxy polymer, a crosslinked carbohydrate, polyester, polyanhydride, polyamide, polyether, polyphosphoester, polyorthoester, poly($\varepsilon$-caprolactone) (PCL), or poly(ethylene glycol) (PEG).

13. The method of claim 1, wherein a time at which the outer casing is configured to dissolve is based on a thickness of and a degree of crosslinking within a material of the outer casing.

14. An ingestible electrical device configured to:
following a dissolution of an outer casing, expand a form factor of one or more electrodes comprising a biocompatible conducting material and a biocompatible insulating material, wherein the dissolution occurs in an organism that ingests the outer casing;
activate, based on exposure to an aqueous environment in the organism, a generator connected to the one or more electrodes;
following activation of the generator, deliver one or more of a current or a voltage across the one or more electrodes;
stimulate, based on delivery of the one or more of the current or the voltage, one or more internal cells of the organism that ingests the outer casing; and
cease to deliver the one or more of the current or the voltage across the one or more electrodes after a predetermined time, wherein the one or more electrodes and the generator are configured to break down following the cease to deliver the one or more of the current or the voltage across the one or more electrodes.

15. The ingestible electrical device of claim 14, further configured to:
cause, based on stimulating the one or more internal cells of the organism, a decrease in an amount of intestinal motility in the organism relative to an amount of intestinal motility in the organism prior to the stimulating.

16. The ingestible electrical device of claim 14, further configured to:
stimulate one or more internal cells of a gastrointestinal tract of the organism.

17. The ingestible electrical device of claim 14, wherein the biocompatible conducting material comprises at least one of a bioinert metal or a conducting polymer.

18. The ingestible electrical device of claim 17, wherein the bioinert metal comprises at least one of copper, gold, magnesium, silver, platinum, or zinc.

19. The ingestible electrical device of claim 14, wherein the biocompatible insulating material comprises a bioexcretable copolymer.

20. The ingestible electrical device of claim 19, wherein the bioexcretable copolymer comprises at least one of polyester, polyanhydride, polyamide, polyether, polyphosphoester, polyorthoester, poly($\varepsilon$-caprolactone) (PCL) or poly(ethylene glycol) (PEG).

21. The ingestible electrical device of claim 14, wherein the generator comprises a water-activated battery comprising biocompatible materials.

22. The ingestible electrical device of claim 14, wherein the generator comprises a receiver coil and a rectifying circuit, each of the receiver coil and the rectifying circuit comprising one or more of a biodegradable material and a bioinert metal, the receiver coil configured to receive a near-field radio frequency signal, and the rectifying circuit configured to convert energy from the near-field radio frequency signal into the one or more of the current or the voltage.

23. The ingestible electrical device of claim 14, wherein the generator comprises one or more fuel cells.

24. The ingestible electrical device of claim 14, wherein the generator is configured to provide up to 0.1 mA of current for up to 90 minutes.

25. The ingestible electrical device of claim 14, wherein the outer casing comprises at least one of a gelatin material, a synthetic alphahydroxy polymer, a crosslinked carbohydrate, polyester, polyanhydride, polyamide, polyether, polyphosphoester, polyorthoester, poly($\varepsilon$-caprolactone) (PCL), or poly(ethylene glycol) (PEG).

26. The ingestible electrical device of claim 14, wherein a time at which the outer casing is configured to dissolve is based on a thickness of and a degree of crosslinking within a material of the outer casing.

* * * * *